United States Patent
Giakos

(10) Patent No.: US 7,428,050 B2
(45) Date of Patent: *Sep. 23, 2008

(54) MULTISPECTRAL, MULTIFUSION, LASER-POLARIMETRIC OPTICAL IMAGING SYSTEM

(75) Inventor: George C. Giakos, Akron, OH (US)

(73) Assignee: The University of Akron, Akron, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 10/560,293

(22) PCT Filed: May 13, 2004

(86) PCT No.: PCT/US2004/015046

§ 371 (c)(1),
(2), (4) Date: Mar. 21, 2006

(87) PCT Pub. No.: WO2005/029015

PCT Pub. Date: Mar. 31, 2005

(65) Prior Publication Data

US 2006/0164643 A1 Jul. 27, 2006

Related U.S. Application Data

(60) Provisional application No. 60/482,386, filed on Jun. 25, 2003.

(51) Int. Cl.
*G01J 4/00* (2006.01)

(52) U.S. Cl. ...................................... 356/369; 356/364

(58) Field of Classification Search .......... 356/364–370
See application file for complete search history.

(56) References Cited

U.S. PATENT DOCUMENTS

| | | | |
|---|---|---|---|
| 5,129,724 A * | 7/1992 | Brophy et al. | 356/503 |
| 5,247,176 A | 9/1993 | Goldstein | |
| 5,788,632 A * | 8/1998 | Pezzaniti et al. | 600/316 |
| 6,316,773 B1 | 11/2001 | Giakos | |
| 6,384,916 B1 * | 5/2002 | Furtak | 356/369 |
| 6,618,145 B1 * | 9/2003 | Goldstein et al. | 356/369 |
| 6,636,582 B2 | 10/2003 | Rader et al. | |
| 6,683,934 B1 | 1/2004 | Zhao et al. | |
| 6,762,829 B2 * | 7/2004 | Babin et al. | 356/73.1 |
| 6,927,888 B2 * | 8/2005 | Garcia et al. | 359/196 |
| 7,061,614 B2 * | 6/2006 | Wang et al. | 356/369 |
| 2004/0012853 A1 | 1/2004 | Garcia et al. | |

* cited by examiner

*Primary Examiner*—L. G. Lauchman
*Assistant Examiner*—Jarreas C Underwood
(74) *Attorney, Agent, or Firm*—Roetzel & Andress; George W. Moxon II

(57) ABSTRACT

In one embodiment, the present invention is directed to a multi-energy polarization imaging method consisting of a multi-fusion, dual-rotating retarder/multiple-energy complete Mueller matrix-based polarimeter and dual-energy capabilities. By subtracting polarimetric parameters such as degree of polarization, degree of linear polarization, degree of circular polarization, respectively, obtained with interrogation light beams of wavelengths $\lambda_1$, and $\lambda_2$, the system of the present invention can obtain, in one embodiment, enhanced imaging.

16 Claims, 5 Drawing Sheets

MULTISPECTRAL, MULTIFUSION, LASER-POLARIMETRIC OPTICAL IMAGING SYSTEM

RELATED APPLICATIONS

This application claims the benefit of U.S. Provisional Application No. 60/482,386, filed Jun. 25, 2003.

FIELD OF THE INVENTION

The invention relates generally to optical-imaging systems, and more particularly to a multi-fusion, dual-rotating retarder/multiple-energy complete Mueller matrix-based polarimeter. The proposed imaging system is based on multi-wavelength laser-polarimetric interrogation of targets surrounded by scattered media or any media in general, using the Mueller matrices formalism together with dual-energy subtraction techniques. Specifically, the term multifusion describes the use of several imaging functions altogether such as polarimetric imaging, dual-energy subtraction, multifocal imaging, multiple-exposures, and other. By subtracting polarimetric parameters such as degree of polarization (DOP), degree of linear polarization (DOLP), degree of circular polarization, respectively (DCP), obtained with interrogation light beams of wavelengths $\lambda_1$ and $\lambda_2$, he system, enhanced imaging is obtained. The multispectral, multifusion, dual-energy Mueller-based polarimeter system of the present invention can also utilize short-duration optical pulses or snapshots of light pulses providing therefore, temporal information, in addition to the spatial and spectral information of the target. This invention has potential applications for homeland security, defense and battleship, specifically for target identification, recognition, and, surveillance, medical imaging, bioengineering and medical applications, cancer detection, image guided biopsy, and molecular imaging, and nondestructive evaluation of objects, with emphasis on industrial imaging.

BACKGROUND OF THE INVENTION

Optical imaging and target detection through scattering media have been studied for use in aerospace, medical, military, and industrial applications. Conventional polarimetric-imaging techniques rely on the assumption that weakly scattered light maintains its initial polarization state, while highly scattered light does not. The, the polarization of scattered light actually depends upon a number of geometrical, and physical parameters.

The intensity of an image captured by interrogating a target with laser light can be altered by varying the polarization state of the incident laser light and changing the configuration of an analyzer to receive different polarization components of the backscattered light. Previous attempts to generate images based on the polarization state of backscattered light have focused on the loss of linear polarization through light-scattering media as detected by the analyzer. However, linear-polarized light tends to lose a significant degree of polarization in a large number of light-scattering media. Such attempts have failed to analyze the depolarization of circularly-polarized light, based on the Mueller-matrix concept, by detecting highly-scattered light from biologically-inspired phantoms as well as, to a lesser extent, from biological tissues.

Other approaches have been designed to enhance the appearance of images captured using optical imaging techniques. For example, enhancement of such images has been obtained by means of dual-energy imaging principles. The principles of dual-energy imaging involve the use of two optical images, one produced by interrogating the target with a high energy (low wavelength) light source, and another produced by interrogating the target with a low energy (high wavelength) light source. The target typically reflects the high-energy light differently than it does the low-energy light. A weighted subtraction of these two images can produce a sharply-contrasted digital image which minimizes the appearance of interfering background structures.

An additional technique known for enhancing imaging applications is the use of focal-length scanning devices. Focal length scanning of the target is performed by varying the focal depth of a lens positioned to direct the light used for interrogating the target. This essentially illuminates a single "slice" of the target located a predetermined distance from the lens in the axial direction of the propagating light. The process is continuously repeated for several different focal depths until the entire three-dimensional target has been captured as an image. But again, this hardware-based super-resolution approach does not provide a desirable contrast between the target and interfering background noise.

Several studies have been conducted to evaluate the exploitation of a dual-rotating retarder complete-Mueller polarimeter. However, none of these studies have fused dual-energy capabilities with polarimetric measurements. Furthermore, there exist other studies involving the exploitation of dual-rotating polarizer incomplete polarimeter configuration for aerospace, and medical imaging applications. But since the polarimeters involved in these studies are incomplete, they do not take into account elliptical polarization states. And again, these studies do not contemplate the fusion of dual-energy techniques with polarimetric imaging principles. Finally, the exploitation of polarization principles fused with dual-energy capabilities has been proposed, but such proposals have all neglected to incorporate the means of dual-rotating retarder complete polarimeter.

Accordingly, there is a need in the art for an imaging system that can yield improved images with reduced noise, high specificity, and high contrast. The system should be a complete polarimeter and analyze the depolarization of circularly-polarized light, based on the Mueller-matrix concept, by detecting highly-scattered light from biologically-inspired phantoms as well as from biological tissues. Such a system should provide enhanced imaging capabilities for homeland security, biomedical, industrial, aerospace applications. Further, the optical fusion sensor system should possess imaging capabilities over a wide spectral bandwidth, while providing a desirable battleship awareness by rapid detection, location and recognition of enemy targets in highly cluttered environments. In addition, the system should be combinable with an active or passive multispectral spectropolarimeter or multispectral imaging system for enhanced imaging, and should prove useful should exhibit improved performance in adverse atmospheric and ambient environmental conditions.

SUMMARY OF THE INVENTION

It is an objective of the invention to maximize the contrast of images captured for a variety of imaging applications.

The present invention achieves this and other objectives by providing an imaging system and method for generating a multi-energy image of a target by subtracting unwanted interfering structures from the target image and analyzing the polarization state of light that has interacted with the target.

In accordance with one aspect, the present invention provides a multi-energy polarization imaging system including a light source for illuminating a target with a first quantity of light having a first wavelength and a second quantity of light having a second wavelength, wherein the second wavelength is different than the first wavelength. A polarization-state generator generates a polarization state for each of the first and second quantities of light, and includes a first polarizer through which the first and second quantities of light are transmitted before entering a first waveplate. A polarization-state receiver evaluates a resulting polarization state of the first and second quantities of light following illumination of the target, the polarization-state receiver including a second waveplate through which the first and second quantities of light are transmitted before entering a second polarizer. An optical image-capture device captures a first image of the target illuminated by the first quantity of light and a second image of the target illuminated by the second quantity of light. A processing unit assigns a weighting factor to at least one of the first and second images and evaluates a weighted difference between the first and second images to generate a multi-energy image of the target.

In accordance with another aspect, the present invention also provides a method for generating a multi-energy image of a target, the method including the steps of emitting a first quantity of light having a first wavelength and a second quantity of light having a second wavelength that is different than the first wavelength; creating an initial polarization state for each of the first and second quantities of light by polarizing and then retarding one component of each of the first and second polarized quantities of light relative to another component of the first and second quantities of light; and directing the polarization state for each of the first and second quantities of light generally toward the target. The method further includes the steps of analyzing a resulting polarization state for each of the first and second quantities of light by retarding one component of the first and second quantities of light following illumination of the target relative to another component of the first and second quantities of light, and then polarizing the retarded first and second quantities of light; capturing a first image of the target illuminated by the first quantity of light and a second image of the target illuminated by the second quantity of light; weighting at least one of the first and second images; and generating the multi-energy image of the target by evaluating a weighted difference between the first and second images.

BRIEF DESCRIPTION OF THE DRAWINGS

The foregoing and other features and advantages of the present invention will become apparent to those skilled in the art to which the present invention relates upon reading the following description with reference to the accompanying drawings, in which.

DETAILED DESCRIPTION OF PREFERRED AND ALTERNATE EMBODIMENTS

Figure 1:
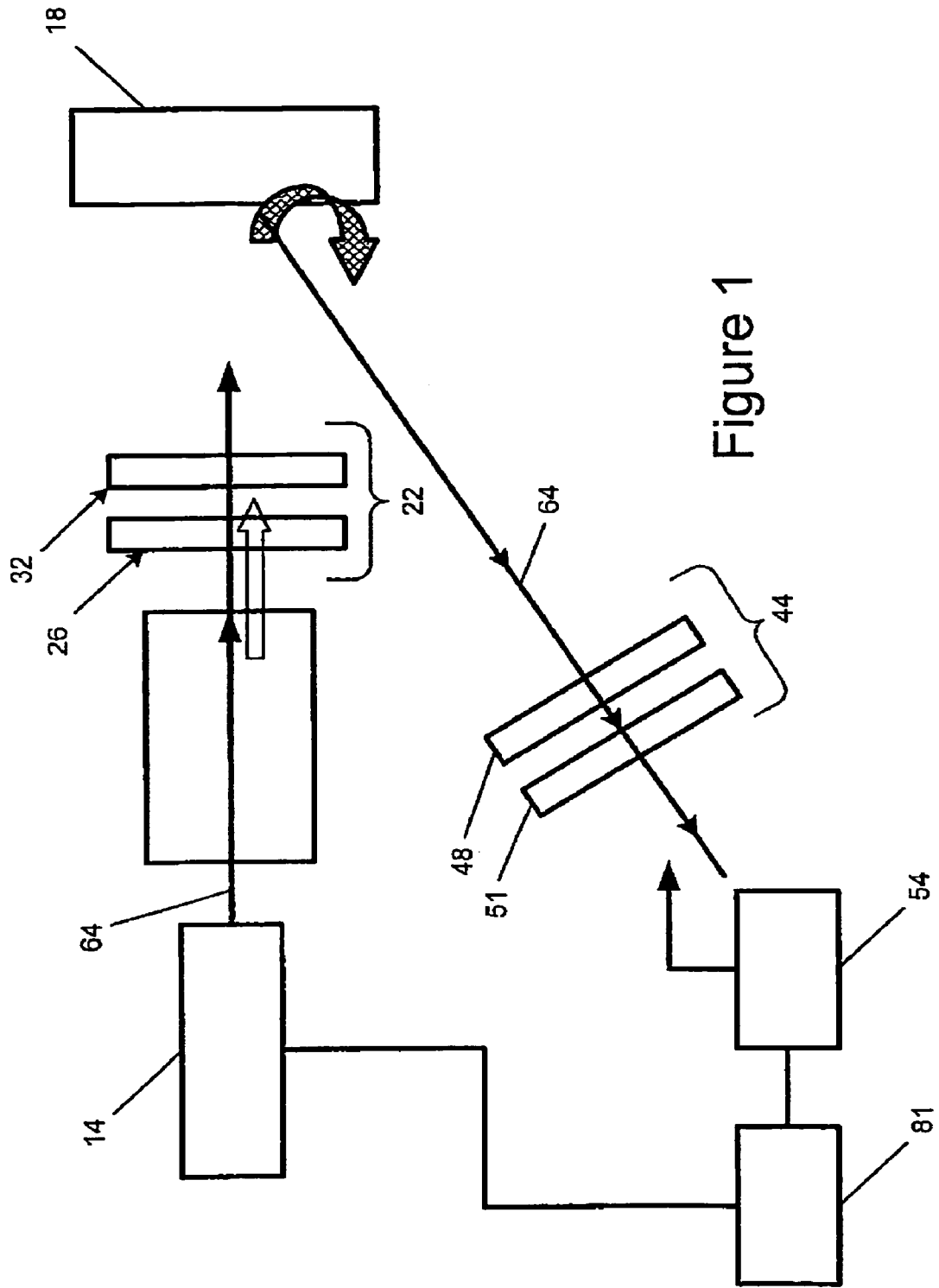
FIG. 1 is a schematic representation of a multispectral, multifusion, dual-energy Mueller-based optical imaging system in accordance with the present invention configured in a backscattered mode.

Certain terminology is used herein for convenience only and is not to be taken as a limitation on the present invention. Further, in the drawings, certain features may be shown in somewhat schematic form.

FIG. 1 illustrates one embodiment of a multi-energy polarization imaging system 10 according to the present invention. The imaging system 10 includes a light source 14 for illuminating a target 18 with a first quantity of light having a first wavelength and a second quantity of light having a second wavelength. The second wavelength is different than the first wavelength to produce a high-contrast image. A polarization-state generator 22 is provided for generating a polarization 22 state for each of the first and second quantities of light. The polarization-state generator includes a first polarizer 26 through which the first and second quantities of light are transmitted before entering a first waveplate 32, which creates a phase difference between an ordinary component 36 (FIG. 3) and an extraordinary component 42 (FIG. 3) of the polarized first and second quantities of light. A polarization-state receiver 44 is positioned to evaluate a resulting polarization state of the first and second quantities of light following illumination of the target 18, the polarization-state receiver 44 including a second waveplate 48 through which the first and second quantities of light are transmitted before entering a second polarizer 51. An optical image-capture device, such as a charge-coupled device ("CCD"), photo-electronic camera, CMOS detector, and the like, captures a first image of the target illuminated by the first quantity of light and a second image of the target illuminated by the second quantity of light. A processing unit 57 assigns a weighting factor to at least one of the first and second images and evaluates a weighted difference between the first and second images to generate a multi-energy image of the target 18.

Figure 4:
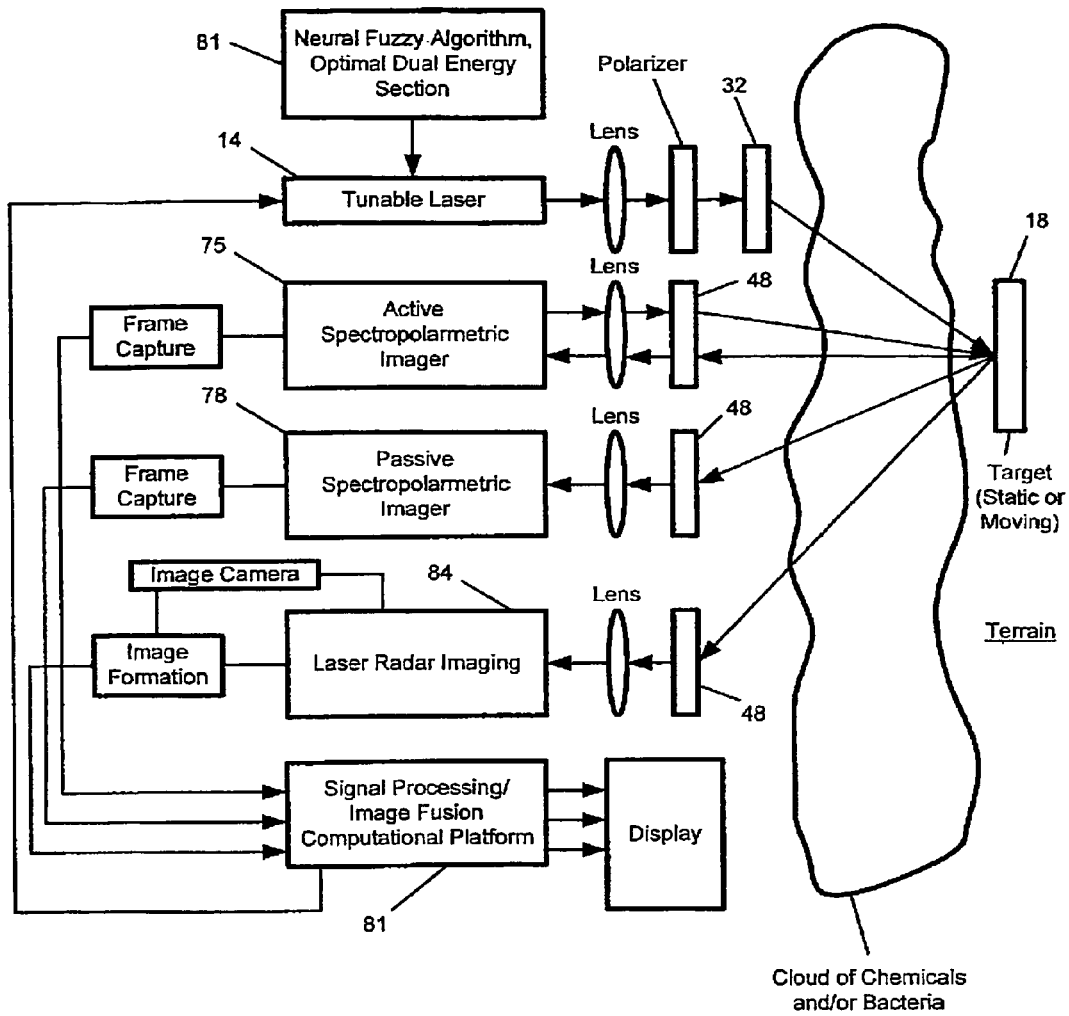
FIG. 4 is a block diagram of a multispectral, multifusion, dual-energy Mueller-based optical imaging system in accordance with the present invention implemented with an active multispectral spectropolarimeter, a passive multispectral spectropolarimeter, and a laser radar system.

The imaging system 10 of the present invention fuses dual-energy imaging principles with polarimetric imaging principles, optionally at varying focal depths and exposures, to generate and display a high-contrast image. The interrogation of a target 10 with two or more quantities of light having different wavelengths (multispectral interrogation), and the acquisition of polarimetric images by applying dual-rotating quarter-wave linear-retarder complete-polarimeter techniques, allows one to obtain enhanced polarimetric signatures by subtraction of the polarization parameters of the acquired images, such as degree of polarization (DOP), degree of linear polarization (DOLP), degree of circular polarization (DOCP), ellipticity, azimuth, and eccentricity, or their differences such as DOP difference, DOLP, difference, DOCP difference, obtained at different wavelengths. This will maximize the signal-to noise ratio of the target images. The imaging system 10 of the present invention can be combined with an active or passive multispectral spectropolarimeter 75, 78 (FIG. 4) or multispectral/hyperspectral imaging system for enhanced imaging, as well as with white light sources, partially polarized sources, multiple exposures, and the like. As a result, a multiwavelength, multifusion optical imaging system 10 with enhanced contrast and specificity can be obtained. In addition, the system 10 can be operated as a monostatic polarimetric laser reflectometer, as a bistatic polarimeter laser reflectometer, or as a network of several polarimeters (FIG. 5) operating in reflection or transmission mode, or any combination of these modes. It can also be implemented with super-resolution techniques (variable focus lenses, or algorithms), as well provide imaging information at variable depths (axial direction along a focal axis in which the light propagates), either by translating the target along the focal-axis, via a computerized translational motorized stage, or utilizing standard confocal microscopy techniques. As a result, polarized multiwavelength planar image sections, at the longitudinal directions can be obtained.

Although described herein as a dual-energy imaging system, it should be understood that the system 10 of the present invention can be used to generate and display any multi-energy image. Instead of being limited to two quantities of light, a plurality of light quanitites, described interchangeably herein as beams of light, laser light beams, and laser beams, each having a different wavelength, are used to illuminate the target 18 for capturing images of the target 18. Regardless of the number of different wavelengths used for illumination purposes, the principles of multiple-energy imaging involve the use of two or more optical images to generate a multi-energy image. A first image is captured by illuminating the target 18 with light having the first wavelength, and at least one more image is captured by illuminating the target 18 with light having a second wavelength that is different than the first wavelength. Optionally, this can be performed with a quantity of light having a high energy (short wavelength) and another quantity of light having a low energy (long wavelength) light source.

The terms high and low, and short and long used with reference to the wavelengths of the light for illuminating the target 18 are relative terms that are ordinarily open to subjective interpretation. As used herein, however, the terms high and low, and short an long are relative to the other light wavelengths used to illuminate the target 18. For example, a first quantity of light having high energy level, means that the first quantity of light has an energy level that is higher than the energy level of the second quantity of light. Similarly, if the first quantity of light is described as having a short wavelength, this is used to limit the wavelength of the first quantity of light as being shorter than the wavelength of the second quantity of light.

A weighted subtraction of these two images produces a multi-energy image which minimizes interfering background structures. A weighting factor is assigned to at least one polarization parameter of one or more of the captured images such that the desired contrast is achieved in the multi-energy image generated by evaluating a difference between the images of the target 18 illuminated with the quantities of light having different wavelengths. By weighting at least one of the polarization parameters of an image of the target illuminated at a given wavelength, a suitable amount of undesired interfering objects possibly obstructing the target 18 can be removed from the multi-energy image. For instance, the target 18 and its ambient environment or background can exhibit poor optical contrast due to similar reflectance properties for light at a first wavelength, while the background is the dominant reflective entity at a second wavelength. Capturing a first image of the target 18 and background illuminated by light having the first wavelength and a second image of the target 18 and background illuminated by light having the second wavelength, and then subtracting the background-dominant second image from the first image results in a high contrast multi-energy image of the target 18.

Multi-energy images of the present invention can be one dimensional, two dimensional, and three dimensional. Further, the optical image-capture device 54 can rely on homodyne, heterodyne, superheterodyne detection principles, image intensifiers, photomultipliers, semiconductor detectors, including but not limited to the use of auto balanced detectors and lock-in amplifiers.

Examples of the polarization parameters of the captured images that can be weighted for subtraction from the corresponding polarization parameters of another image captured by illuminating the target 18 at a different wavelength include: degree of polarization ("DOP"), degree of linear polarization ("DOLP"), degree of circular polarization ("DOCP"), ellipticity, azimuth, eccentricity, and the like. The weighted subtraction can also be performed using sets of images, in which case the subtraction will performed on the differences of the sets such as DOP difference, DOLP difference, DOCP difference, ellipticity difference, azimuth difference, eccentricity difference and the like.

Further enhancement is obtained by employing applied polarimetric techniques, and optionally, by also employing focal-length scanning of the object. Focal-length scanning of the target 18 is obtained by varying the focal depth of a lens positioned in front of the target 18 to focus the light so that it converges at a suitable depth within the target 18. This illuminates a single "slice" of the target 18 located a predetermined distance from the lens in the axial direction in which the light propagates. The process is continuously repeated for several different focal depths until the desired portion of the three-dimensional target 18 has been captured as an image.

Figure 2:
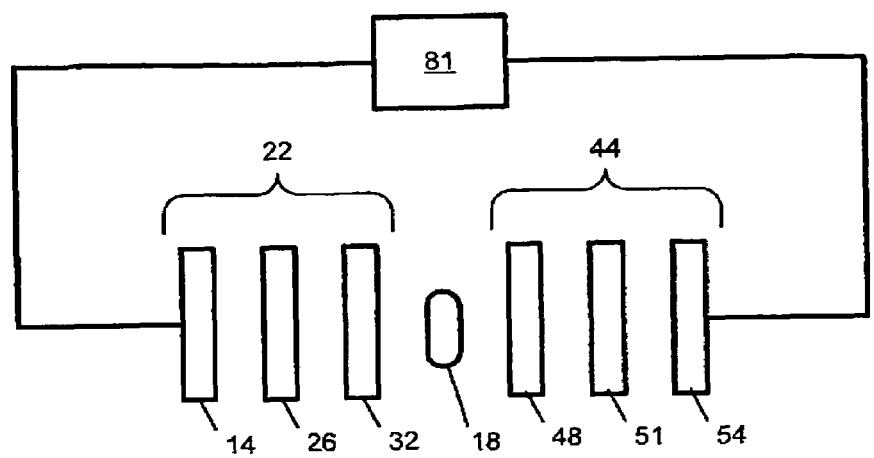
FIG. 2 is a schematic representation of a multispectral, multifusion, dual-energy Mueller-based optical imaging system in accordance with the present invention configured in a transmission mode.

A dual-rotating retarder is positioned adjacent to respective polarizers to form a polarization-state generator 11 and a polarization-state receiver 44 for generating and analyzing, respectively, the polarization state of the first and second quantities of light. The polarization-state generator 22 and receiver 44 operate in conjunction with dual-energy imaging techniques described above. It can be configured to operate in a transmission mode, as shown in FIG. 2, and a backscattered mode as shown in FIG. 1. The adaptability of the present invention allows it to be used in a variety of applications including, but not limited to, medical, aerospace and industrial. For example, the imaging system 10 of the present invention can be used in adverse atmospheric conditions for both air-to-ground and ground-to-ground combat applications. Additionally, the imaging system 10 can be adapted for use in diagnosing medical disease by generating enhanced images of the internal cavity of a patient.

Figure 3:
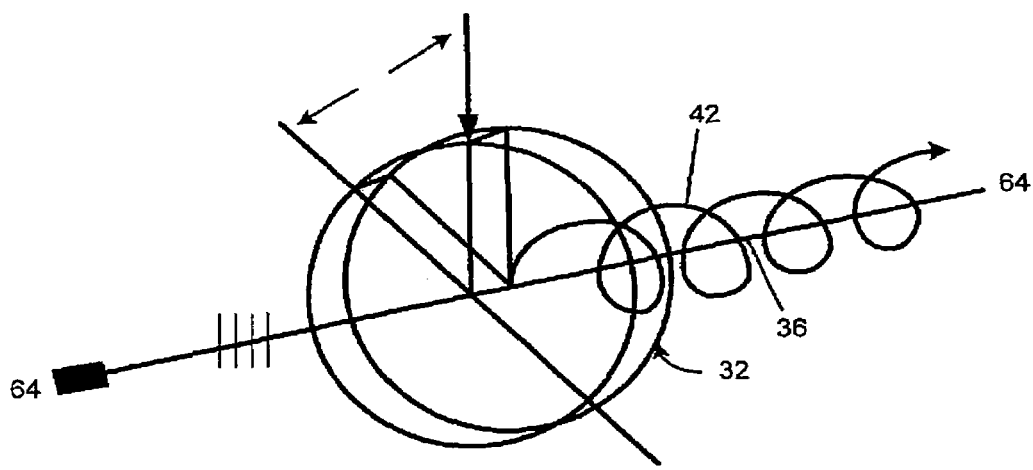
FIG. 3 is a schematic illustration of a quarter-wave retarder in accordance with the present invention.

An exemplary configuration a waveplate forming a portion of the dual-rotating retarder of the polarization-state generator 22 and the polarization-state receiver 44 in the present system is shown in FIG. 3. Polarization states are generated by placing the polarization-state generator 22 in optical alignment along the optical axis 64. Arranged in this manner, the light source 14 emits light that is polarized by the first polarizer 26 and subsequently transmitted through a first waveplate 32. The polarization state of light transmitted from the first waveplate 32 is then analyzed by the polarization-state receiver 44 after the light transmitted from the first waveplate 32 has illuminated the target 18.

Similar to the polarization-state generator 22, the polarization-state receiver 44 includes a second waveplate 48 and a second polarizer 51. Unlike the polarization-state generator 22, however, the polarization-state receiver 44 is arranged such that light illuminating the target is transmitted through the second waveplate 48 prior to being received by the second polarizer.

The first and second waveplates 32, 48 in one embodiment are rotatably supported between the first and second polarizers 26, 51 along the optical path 64 traveled by the light from the light source 14. Rotating the second waveplate 48 at an angular-velocity ratio of 5:1 relative to the first waveplate 32 encodes the 16 parameters of the target's Mueller matrix, which is discussed in detail below, onto the Fourier components of the detected signal. Further, the first and second waveplates 32, 48 are positioned on opposite sides of the target 18, which means that the light used to illuminate the target 18 interacts with the target 18 between interactions with the first and second waveplates 32, 48. This does not require the first and second waveplates 32, 48 to be linearly aligned, but merely positioned along the optical path 64 traveled by the light from the light source 14 to the optical image-capture device 54. Thus, the system 10 can be arranged in a linear arrangement as shown in FIG. 2, or a backscattering mode as shown in FIG. 1.

The waveplates 32, 48 of the present invention, also known as retardation plates and phase shifters, are made from materials which exhibit birefringence. The velocities of ordinary and extraordinary light rays 36, 42 through the birefringent materials vary inversely with their refractive indices. The phrase "ordinary ray" is commonly used to refer to the component of the light incident on the waveplate 32, 48 that travels quickly through the waveplate material relative to the "extraordinary ray," 42 which travels through the waveplate material relatively slower than the ordinary ray 36. The difference in velocities through the waveplate material gives rise to a phase difference, also referred to as a phase shift, between the ordinary and extraordinary rays 36, 42. The degree of the phase difference introduced by the waveplates 32, 48 is dependent upon the path length through the waveplates 32, 48, which, in the present case, is equal to the thickness of the waveplates 32, 48. Waveplates 32, 48 that introduce a phase shift of between 0 and 90° between the ordinary and extraordinary light components 36, 42 produce elliptically polarized light (i.e., the ordinary and extraordinary components 36, 42 are not equal in length), while a phase shift of exactly 90° produces circularly polarized light where the ordinary and extraordinary components are equal in length. As mentioned above, elliptically and circularly polarized light tend to maintain their polarization more than linearly polarized light through many light-scattering media According to one embodiment of the present invention, the first and second waveplates 32, 48 are sized to introduce a 90° phase shift between the ordinary and extraordinary 36, 42 components of the incident light. Since such a phase shift amounts to one fourth of a complete wave, waveplates 32, 48 of this size are referred to as quarter-wave retarders.

The first and second polarizers 26, 51 are fixed in position, and can be any material that impedes the transmittance of at least one component of light through the polarizer while allowing another component to pass therethrough generally unimpeded. By fixing the position of the first and second polarizers 26, 51, the effect of any instrumental polarization preceding or following the polarizers 26, 51 is minimized. Also, the Fourier transform on the data automatically performs a least squares fit to the undetermined data set. The present system 10 is also resistant to beam wander if measurements are made over a $2\pi$ cycle.

The light source 14 of the present invention can be any suitable device that can emit light energy. According to an embodiment of the present invention, the light source 14 is a tunable laser having a variably adjustable wavelength. By tunable, it is meant that the laser can be tuned to emit laser light having any wavelength within a predetermined range of wavelengths. Other suitable light sources 14 include, but are not limited to, hyperspectral/multispectral light sources, white light, partially polarized light sources, and the like. The multispectral, multifusion, dual-energy Mueller-based polarimeter system 10 of the present invention can also utilize short-duration optical pulses or snapshots of light pulses providing therefore, temporal information, in addition to the spatial and spectral information of the target 18.

Further, the system 10 of the present invention can include a plurality of light sources 14 for illuminating the target 18. The plurality of light sources 14 can each illuminate the target 18 with a quantity of light having a different wavelength, forming an illumination plane or point on the target. By varying one or more of the geometry and the orientation of the light sources 14, a new plane or point of illumination on the target 18 can be established. This variation of the geometry and/or the orientation of the light sources can be repeatedly performed to generate a desired multi-energy image.

Using the present invention for applications such as designing optical tomography systems, for example, the light source 14 can be configured to utilize planar geometry, fan-beam geometry, pointwise illumination, or any combination thereof Pointwise illumination should be provided by any beam steering mirror-like devices such as electromechanical, opto-electronic, acoustiooptic, all optical-based technology, liquid-crystal-based mirror, and any other such devices.

Figure 5:
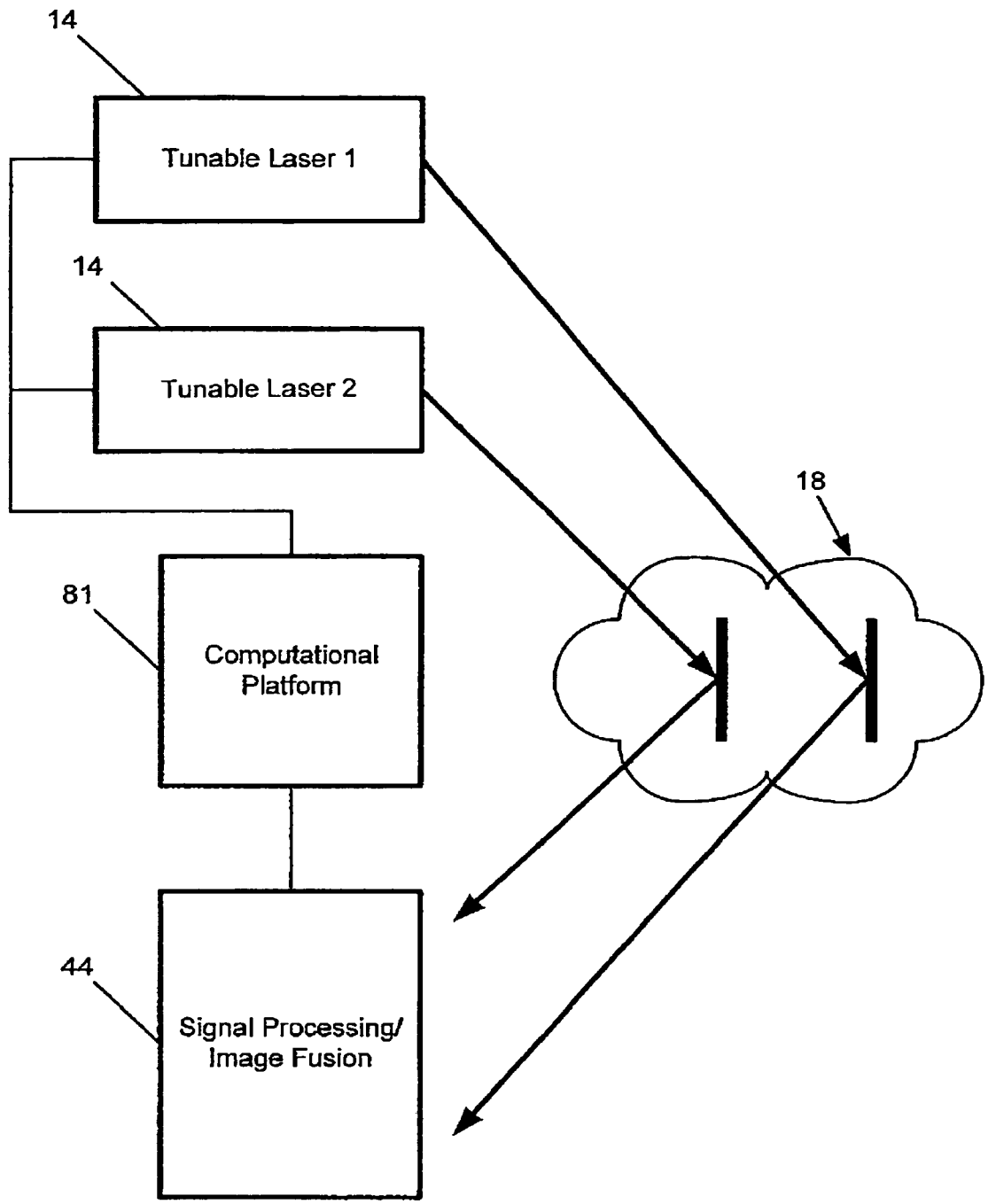
FIG. 5 is an illustrative arrangement of a network of multispectral, multifusion, dual-energy Mueller-based optical imaging systems in accordance with the present invention.

Additionally, an embodiment of the present invention shown in FIG. 5 implements a network comprising a plurality of dual-rotating-retarder complete Mueller-matrix polarimeters, each targeting a different location of the target 18. This embodiment can be implemented by positioning a dual-rotating-retarder complete Mueller-matrix polarimeter imaging system 10 of the present invention at a plurality of locations relative to the target 18. Similar to the individual imaging system 10, each imaging system 10 in the network illuminates the target 18 with two or more quantities of light, each quantity of light having a different wavelength. However, unlike the individual imaging system 10, each imaging system 10 in the network focuses the first and second quantities of light to penetrate the target 18 at different depths or on different surface areas. The weighted subtraction of polarization parameters acquired by illuminating the target 18 with the quantities of light having different wavelengths is performed for each individual imaging system 10 in the network to generate individual multi-energy polarimetric images. Each of these individual images is then communicated to a common computational platform 81 where a composite image of the target 18 is generated from a combination of the individual images. As the network is illustrated in FIG. 5, the polarization-state generator 22 and light source 14 of each individual imaging system 10 are represented generally by the blocks entitled "TUNABLE LASER 1" and "TUNABLE LASER 2". Similarly, the polarization-state receiver and optical-imaging device for each imaging system 10 in the network is represented generally as the block entitled "SIGNAL PROCESSING/IMAGE FUSION." The composite image can be a three-dimensional image of the target 18, a two-dimensional image of the target's surface, or any other type of image. Furthermore, the composite image can be formed by subtracting an individual image of a layer within the target 18 from another individual image of a different layer within the target 18. In this manner, interference from one layer of the target 18 that could obstruct the view of the layer of interest in the target 18 in the composite image is minimized.

The common computational platform 81 can store information concerning the wavelengths of the light emitted by each individual imaging system 10 in a database stored in a computer readable memory for optimizing operation of the network in future applications. An artificial neural network ("ANN"), described in detail below, can be used with the computational platform 81 to select optimal wavelengths for the individual light sources 14 of the network. The optimal wavelengths can depend on a variety of factors such as atmospheric conditions through which the quantities of light are to be transmitted, properties of the target 18 (i.e., whether the target region of interest includes biological tissue, bone structures, gaseous elements, hardened structures, synthetic objects, radioactive materials, etc.), and other factors. Further, similar to the individual imaging systems 10, one or more of the individual imaging systems 10 of the network can be in a fixed position, dynamically positioned in an aircraft, satellite, medical instrumentation, and the like, and include applications for target surveillance and identification, homeland security, air defense, battleship awareness, and other suitable applications. Likewise, the target 18 can be static or dynamic. And again, referring to FIG. 4, the individual imaging systems 10 and the network can be implemented with an active spectropolarimetric imager 75, passive spectropolarimetric imager 78, laser radar imager 84, and any combination thereof.

The necessary computational hardware and software for the operation of the system 10 of the present invention is in operational communication with the features of the system 10 discussed above. The computational platform includes at least a processing unit operatively connected to a computer readable memory. Computer logic stored in the computer-readable memory along with information collected from previous operations of the system 10 and pre-programmed into the computer readable memory allow the system 10 to adaptively select suitable wavelengths for the first and second quantities of light based on at least the ambient environment of the target 18. For example, the computational platform can include what is commonly referred to as an intelligent system, such as an artificial neural network, to determine the optimal wavelengths to be used for target recognition and identification. This can be used to search for targets 18 amidst camouflage nets, trees, fog or other adverse atmospheric conditions, to locate a known composition inside the body of patient in a medical context, and other similar applications.

Generally, an artificial neural network ("ANN") includes highly-interconnected simple computing mathematical nodes, analogous to neurons in a biological neural network. The interconnections between these mathematical nodes (neurons), resembling synapses in biological neural networks, are called weights and provide means to store knowledge. The functional mappings are acquired through a learning process and the knowledge is stored in the form of weights. The leaning process involves repeated training in order to accurately learn the task. Alternately, a database of information can be preprogrammed into the computer-readable memory to minimize the time required for the learning process.

An embodiment of the ANN of the present invention uses a committee of neural networks to increase the reliability of choices made by the ANN. Three or more ANNs are trained with different architecture, initial weights, and the best ANNs are recruited to form a committee for selecting the appropriate light wavelengths. Inexact-reasoning techniques such as fuzzy logic can be employed to further enhance the system.

In use, the system 10 illustrated in FIG. 1 yields a complete measurement of all sixteen Mueller matrix elements through the Fourier analysis of the detected signal. The qth measurement of the irradiance measurement is described by the Mueller matrix equation for the system as, $$\vec{S}_{out}(q) = M_{sys}$$
$$\vec{S}_{in} = M_{LP2} M_{LR2}(q) M_{sample} M_{LR1}(q) M_{LP1}(q) \vec{S}_{in} \quad (1)$$

where $S_{out}(q)$ and $S_{in}$ are the Stokes parameters at the exit and entrance of the system respectively; $M_{LP1}$ and $M_{LP2}$ are the Mueller matrices of ideal polarizers 26, 51 with their transmission axis 64 oriented along the horizontal x direction, and $M_{LR1}(q)$ and $M_{LR2}(q)$ are the Mueller matrices of the quarter-wave retarders 32, 48 in the polarization-state generator 22 and the polarization-state receiver 44. In general, $$M_{LP1} = M_{LP2} = \frac{1}{2}\begin{pmatrix} 1 & 1 & 0 & 0 \\ 1 & 1 & 0 & 0 \\ 0 & 0 & 0 & 0 \\ 0 & 0 & 0 & 0 \end{pmatrix} \quad (2)$$

$$M_{LR1} = \begin{pmatrix} 1 & 0 & 0 & 0 \\ 0 & \cos^2 2\gamma q & \sin 2\gamma q \cos 2\gamma q & -\sin 2\gamma q_0 \\ 0 & \cos 2\gamma q \sin 2\gamma q & \sin^2 2\gamma q & \cos 2\gamma q \\ 0 & \sin 2\gamma q & -\cos 2\gamma q & 0 \end{pmatrix} \quad (3)$$

$$M_{LR2} = \begin{pmatrix} 1 & 0 & 0 & 0 \\ 0 & \cos^2 10\gamma q & \sin 10\gamma q \cos 10\gamma q & -\sin 10\gamma q_0 \\ 0 & \cos 10\gamma q \sin 10\gamma q & \sin^2 10\gamma q & \cos 10\gamma q \\ 0 & \sin 10\gamma q & -\cos 10\gamma q & 0 \end{pmatrix} \quad (4)$$

$$M_{sample} = \begin{pmatrix} m_{11} & m_{12} & m_{13} & m_{14} \\ m_{21} & m_{22} & m_{23} & m_{24} \\ m_{31} & m_{32} & m_{33} & m_{34} \\ m_{41} & m_{42} & m_{43} & m_{44} \end{pmatrix}, \quad (5)$$

Substituting (2)-(5) into (1) and carrying out the appropriate trigonometric transformations, one can show that the output irradiance is given by the first element of the output Stokes vector, $S_{0,out}(q)$. The expression for the measured irradiance is expanded and rewritten to produce terms that correspond to the Fourier series expansion $$s_{0,out}(q) = I_q = \frac{a_0}{2} + \sum_{n=1}^{12}(a_n \cos 2n\gamma q + b_n \sin 2n\gamma q) \quad (6)$$

where $I_q$ is the measured irradiance, and the Fourier coefficients are a function of the sixteen elements of the sample Mueller matrix. These expressions can be inverted to offer Mueller matrix elements in terms of the Fourier series coefficients. Overall, the addition of polarization imaging capabilities results in a significant enhancement in contrast. This is particularly true for dark structures such as tumors, which minimize optical or near infrared detectability. Percent polarization of diffuse light increases with decreasing surface reflectance. As a result, a dark structure with a reflectance of 2% exhibits a percentage polarization of approximately 100%.

The principles of dual-energy imaging involve the use of two optical images, one produced from a high energy (low wavelength) and another from a low energy (high wavelength) coherent light source. A weighted subtraction of these two images can produce a digital image which eliminates interfering background structure. By adding polarization imaging capabilities to the dual-energy system, a multi-fusion optical imaging system with enhanced imaging capabilities can be obtained.

In fact, a subtraction of the polarimetric image acquired at one wavelength by that acquired at the other polarimetric image leaves only the absorption dependent factor, yielding the following expression:

$$R(t) = \log_e\left\{\frac{I[(\mu_a(\lambda_1)]}{I[(\mu_a(\lambda_2)]}\right\} = \Delta\mu_a z \quad (7)$$

where $\Delta\mu_a = \mu_a(\lambda_2) - \mu_a(\lambda_1)$ (8)

More generally, however, the subtraction equations of the present invention can be expressed as:

$(DOP)_{\lambda 1} - (DOP)_{\lambda 2}$ (8)

$(DOLP)_{\lambda 1} - (DOLP)_{\lambda 2}$ (9)

$(DOCP)_{\lambda 1} - (DOCP)_{\lambda 2}$ (10)

$(e)_{\lambda 1} - (e)_{\lambda 2}$ (11)

$(\eta)_{\lambda 1} - (\eta)_{\lambda 2}$ (12)

$(\epsilon)_{\lambda 1} - (\epsilon)_{\lambda 2}$ (13)

where DOP, DOLP, DOCP, are abbreviations for the degree of polarization, degree of linear polarization, degree of circular polarization, respectively, obtained with interrogation light beams of wavelengths $\lambda_1$ and $\lambda_2$, given as $$DOP = \frac{(S_1^2 + S_2^2 + S_3^2)^{1/2}}{S_0} \quad (14)$$

$$DOLP = \frac{(S_1^2 + S_2^2)^{1/2}}{S_0} \quad (15)$$

$$DOCP = \frac{S_3}{S_0} \quad (16)$$

$$e = \frac{b}{a} = \frac{s_3}{s_0 + \sqrt{s_1^2 + s_2^2}} \quad (17)$$

$$\eta = \frac{1}{2}\arctan\left[\frac{s_2}{s_1}\right] \quad (18)$$

$$\varepsilon = \sqrt{1 - e^2} \quad (19)$$

and e, $\eta$, and $\epsilon$ are the ellipticity, azimuth, and eccentricity, respectively, obtained with interrogation light beams of wavelengths $\lambda_1$ and $\lambda_2$. Naturally, multiple wavelengths can be utilized to interrogate the target, giving rise to multiple dual-energy difference pairs.

Figure 6:
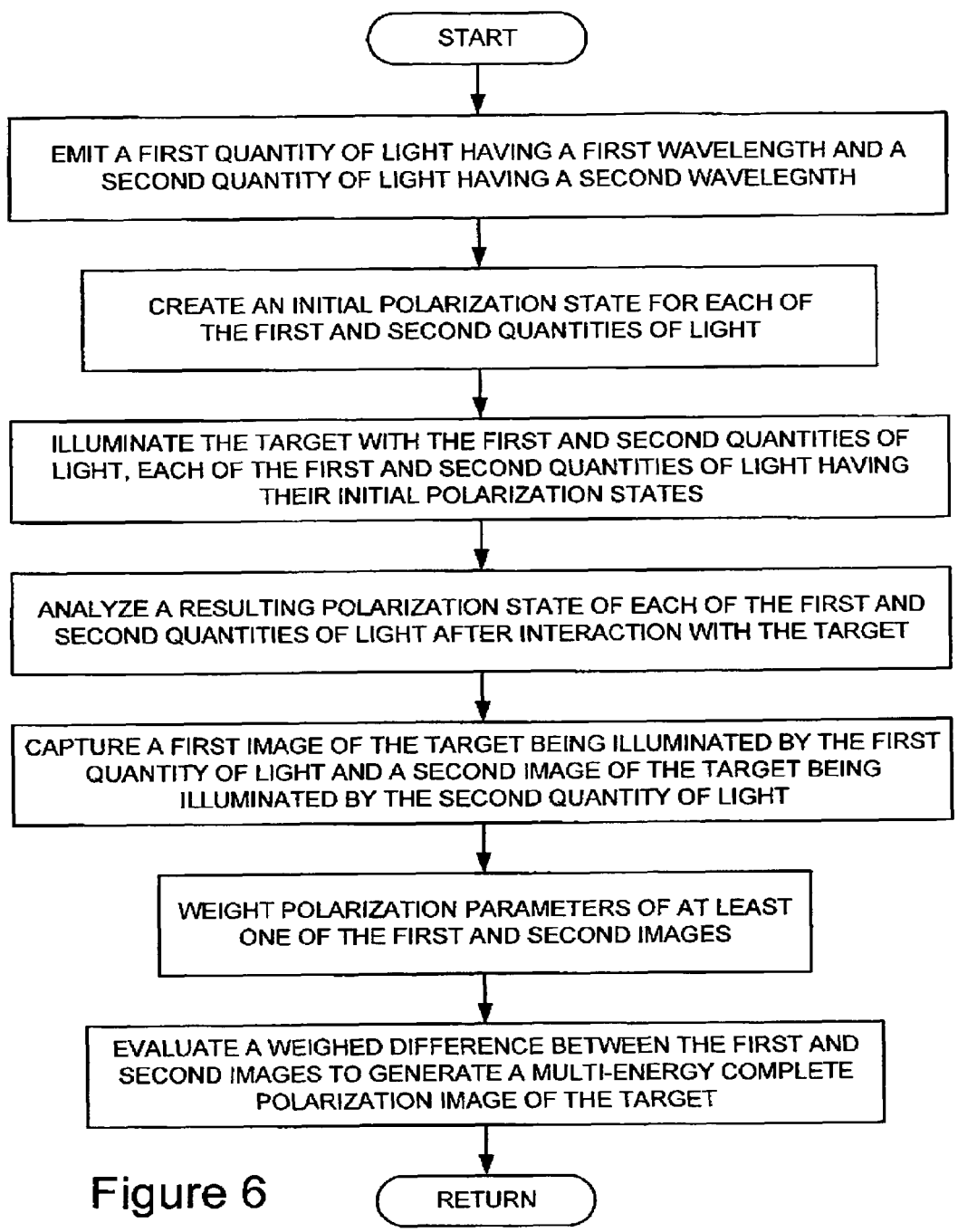
FIG. 6 is a flow diagram of an embodiment of a method for generating a multi-energy image in accordance with the present invention.

In use, with reference to FIG. 6, the multispectral, multi-fusion, dual-energy Mueller-based polarimeter imaging system 10 of the present invention can generate enhanced multi-energy images according to a method of the illustrative embodiment. This illustrative method includes the steps of emitting a first quantity of light having a first wavelength 101 and a second quantity of light having a second wavelength that is different than the first wavelength, creating an initial polarization state for each of the first and second quantities of light by polarizing and then retarding one component of each of the first and second polarized quantities of light relative to another component of the first and second quantities of light 104, and directing the polarization state for each of the first and second quantities of light generally toward the target 107. The method of the illustrative embodiment further includes analyzing a resulting polarization state for each of the first and second quantities of light by retarding one component of the first and second quantities of light following illumination of the target 18 relative to another component of the first and second quantities of light 110, and then polarizing the retarded first and second quantities of light 110; capturing a first image of the target 18 illuminated by the first quantity of light and a second image of the target 18 illuminated by the second quantity of light 113; weighting at least one of the first and second images 116; and generating the multi-energy image of the target by evaluating a weighted difference between the first and second images 119. The weighting factor in some circumstances can be unity, or take on any other value.

The step of creating an initial polarization state 104 includes linearly polarizing the first and second quantities of light. After the linear polarization, at least one of the ordinary and extraordinary components 36, 42 of the linearly-polarized light is retarded with a quarter-wave retarder 32 to create a phase angle between the ordinary and extraordinary components 36, 42.

Similarly, analyzing the resulting polarization state 110 includes analyzing a resulting phase angle between the ordinary and extraordinary components 36, 42 of the first and second quantities of light following interaction of the first and second quantities of light with the target 18. This step evaluates the effect the target 18 has on the polarization state of the first and second quantities of light by transmitting the first and second quantities of light through a second quarter-wave retarder 48 following interaction with the target 18. Then, the first and second quantities of light are again linearly polarized by the second polarizer 51.

Weighting at least one of the first and second images includes 116 the steps of determining a Mueller matrix for each of the first and second images, determining a weighting factor suitable for at least one parameter of the first and second images, and multiplying at least one of the parameters of the first and second images by the value of the weighting factor.

Generating the multi-energy image of the target 119 includes the steps of determining a difference between the at least one weighted image parameter and the remaining image parameter, generating a Mueller matrix for the difference between the two images, and displaying an image generated from the Mueller matrix for the difference between the two images.

Emitting a first quantity of light having a first wavelength and a second quantity of light having a second wavelength 110 includes evaluating an ambient environment of the target 18, comparing the ambient environment of the target 18 to known conditions stored in a computer readable memory, and determining suitable first and second wavelengths based on the comparison between the evaluated ambient environment of the target 18 and the known environments in the computer readable memory using an artificial fuzzy neural network. The ambient environment can be any environment, neighboring object, and the like that can affect the first and second quantities of light en route to the target 18. Nonlimiting examples of such an ambient environment include a gas cloud, fog, or other atmospheric condition through which the first and second quantities of light are transmitted between the light source 14 and the target 18 or other location along the optical path 54 from the light source to the optical image-capture device 54.

From the above description of the invention, those skilled in the art will perceive improvements, changes and modifications. Such improvements, changes and modifications within the skill of the art are intended to be covered by the appended claims.

What is claimed is:

1. A multi-energy polarization imaging system comprising:
a light source for illuminating a target with a first quantity of light having a first wavelength and a second quantity of light having a second wavelength, wherein the second wavelength is different than the first wavelength;
a polarization-state generator for generating a polarization state for each of the first and second quantities of light, the polarization-state generator comprising a first polarizer through which the first and second quantities of light are transmitted before entering a first waveplate;
a polarization-state receiver for evaluating a resulting polarization state of the first and second quantities of light following illumination of the target, the polarization-state receiver comprising a second waveplate through which the first and second quantities of light are transmitted before entering a second polarizer;
an optical image-capture device for capturing a first image of the target illuminated by the first quantity of light and a second image of the target illuminated by the second quantity of light; and
a processing unit for assigning a weighting factor to at least one of the first and second images and evaluating a weighted difference between the first and second images to generate a multi-energy image of the target,
wherein the processing unit comprises an artificial fuzzy neural network that uses information stored in the computer readable memory to determine a suitable wavelength for each of the first and second quantities of light for the conditions at a time when the multi-energy image is to be generated.

2. The system according to claim 1, wherein the optical image capture device is a charge-coupled device.

3. The system according to claim 2, wherein the charge-coupled device is positioned in optical alignment with the polarization-state receiver to capture the first and second images.

4. The system according to claim 1, wherein the light source comprises a laser.

5. The system according to claim 1, wherein the light source is configured to emit light in a planar geometry, fan-beam geometry, pointwise illumination, or any combination thereof.

6. The system according to claim 1, wherein the first and second waveplates are each a quarter-wave retarder.

7. The system according to claim 6, wherein the quarter-wave retarders forming the first and second waveplates are rotated at an angular-velocity ratio of 5:1.

8. The system according to claim 1, wherein the polarization-state generator and the polarization-state receiver are generally linearly aligned on opposite sides of the target.

9. The system according to claim 1, wherein the polarization-state receiver is positioned to evaluate the resulting polarization state of the first and second quantities of light reflected by the target.

10. The system according to claim 1 further comprising a computer readable memory for storing information to be used by the processing unit for determining a suitable wavelength for each of the first and second quantities of light.

11. The system according to claim 1, wherein the optical image-capture device converts the first captured image into a first Mueller matrix of the target and the second captured image into a second Mueller matrix of the target.

12. A method for generating a multi-energy image of a target, the method comprising the steps of:
emitting a first quantity of light having a first wavelength and a second quantity of light having a second wavelength that is different than the first wavelength;
creating an initial polarization state for each of the first and second quantities of light by polarizing and then retarding one component of each of the first and second polarized quantities of light relative to another component of the first and second quantities of light;
directing the polarization state for each of the first and second quantities of light generally toward the target;
analyzing a resulting polarization state for each of the first and second quantities of light by retarding one component of the first and second quantities of light following illumination of the target relative to another component of the first and second quantities of light, and then polarizing the retarded first and second quantities of light;
capturing a first image of the target illuminated by the first quantity of light and a second image of the target illuminated by the second quantity of light;
weighting at least one of the first and second images; and
generating the multi-energy image of the target by evaluating a weighted difference between the first and second images,
wherein the step of generating the multi-energy image of the target comprises the steps of:
determining a difference between the at least one weighted image and the remaining image;
generating a Mueller matrix for the difference between the two images; and displaying an image generated from the Mueller matrix for the difference between the two images.

13. The method according to claim 12, wherein the step of creating an initial polarization state comprises the steps of:
linearly polarizing the first and second quantities of light; and
then retarding at least one of the ordinary and extraordinary components of the linearly-polarized light with a quarter-wave retarder to create a phase angle between the ordinary and extraordinary components.

14. The method according to claim 12, wherein the step of analyzing the resulting polarization state comprises the steps of:
analyzing a resulting phase angle between the ordinary and extraordinary components of the first and second quantities of light following interaction of the first and second quantities of light with the target; and
then linearly polarizing the first and second quantities of light.

15. The method according to claim 12, wherein the step of weighting at least one of the first and second images comprises the steps of:
determining a Mueller matrix for each of the first and second images;
determining a weighting factor suitable for at least one of the first and second images; and
changing at least one of the first and second images by the value of the weighting factor.

16. A method for generating a multi-energy image of a target, the method comprising the steps of:
emitting a first quantity of light having a first wavelength and a second quantity of light having a second wavelength that is different than the first wavelength;

creating an initial polarization state for each of the first and second quantities of light by polarizing and then retarding one component of each of the first and second polarized quantities of light relative to another component of the first and second quantities light;

directing the polarization state for each of the first and second quantities of light generally toward the target;

analyzing a resulting polarization state for each of the first and second quantities of light by retarding one component of the first and second quantities of light following illumination of the target relative to another component of the first and second quantities of light, and then polarizing the retarded first and second quantities of light;

capturing a first image of the target illuminated by the first quantity of light and a second image of the target illuminated by the second quantity of light;

weighting at least one of the first and second images; and generating the multi-energy image of the target by evaluating a weighted difference between the first and second images, wherein the step of generating the multi-energy image of the target comprises the steps of:

determining a difference between the at least one weighted image and the remaining image;

generating a Mueller matrix for the difference between the two images; and displaying an image generated from the Mueller matrix for the difference between the two images.

* * * * *